United States Patent
Vangelisti

(10) Patent No.: US 7,456,290 B2
(45) Date of Patent: Nov. 25, 2008

(54) PROCESS FOR THE PREPARATION OF 2-AMINOMETHYLPYRIDINE DERIVATIVE

(75) Inventor: Manuel Vangelisti, Charvieu-Chavagneux (FR)

(73) Assignee: Bayer Cropscience S.A. (FR)

( * ) Notice: Subject to any disclaimer, the term of this patent is extended or adjusted under 35 U.S.C. 154(b) by 158 days.

(21) Appl. No.: 10/535,723

(22) PCT Filed: Nov. 18, 2003

(86) PCT No.: PCT/EP03/14892

§ 371 (c)(1), (2), (4) Date: May 20, 2005

(87) PCT Pub. No.: WO2004/046114

PCT Pub. Date: Jun. 3, 2004

(65) Prior Publication Data

US 2006/0004206 A1    Jan. 5, 2006

(30) Foreign Application Priority Data

Nov. 20, 2002  (EP)  .................... 02356236

(51) Int. Cl.
*C07D 211/72* (2006.01)
*C07D 211/70* (2006.01)

(52) U.S. Cl. ............ 546/300; 546/314; 546/328; 546/334

(58) Field of Classification Search .......... 546/290, 546/334, 300, 315, 328
See application file for complete search history.

(56) References Cited

FOREIGN PATENT DOCUMENTS

| EP | 0 409 716 | | 1/1991 |
|---|---|---|---|
| JP | 10 101646 | | 4/1998 |
| JP | 10101646 | * | 4/1998 |
| WO | WO 02/16322 | | 2/2002 |
| WO | WO0216322 | * | 2/2002 |
| WO | WO 0216322 | * | 2/2002 |

OTHER PUBLICATIONS

Rylander, Paul, Catalytic Hydrogenation in Organic Synthesis, Academic Press, 1979, p. 140.*
Hcaplus 1906:119496.*
International Search Report dated Apr. 5, 2004.
Patent Abstracts of Japan, vol. 1998, No. 09, Jul. 31, 1998, abstract.
P.N. Rylander, *Hydrogenation Methods* (Best Synthetic Series, published by Academic Press), (1985), p. 148.

* cited by examiner

*Primary Examiner*—Janet L. Andres
*Assistant Examiner*—Binta M Robinson
(74) *Attorney, Agent, or Firm*—Ostrolenk, Faber, Gerb & Soffen, LLP

(57) ABSTRACT

Process for the preparation of 2-aminomethylpyridine derivative of general formula (I) or a salt thereof, formula (I) in which:—n represents 0, 1, 2 or 3,—X is halogen atom,—each Y may be the same or different and may be a halogen atom, a halogenoalkyl, an alkoxycarbonyl or an alkylsulphonyl.

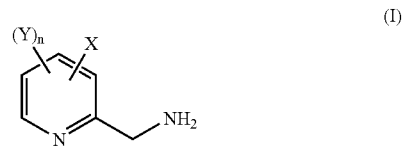

11 Claims, No Drawings

PROCESS FOR THE PREPARATION OF 2-AMINOMETHYLPYRIDINE DERIVATIVE

CROSS REFERENCE TO RELATED APPLICATION(S)

The present application is a 35 U.S.C. §371 national phase conversion of International Application No. PCT/EP2003/014892 filed Nov. 18, 2003, which claims priority of European Patent Application No. 02356236.6 filed Nov. 20, 2002.

The present invention relates to a novel process for the preparation of 2-aminomethylpyridine derivatives which are useful as intermediates for the preparation of pesticides, by catalytic hydrogenation of 2-cyanopyridine derivatives.

Certain catalytic hydrogenation reactions of cyanopyridines to obtain aminomethylpyridines have been disclosed. An additional difficulty exists when the cyanopyridine is substituted by an halogen atom, due to dehalogenation competitive reaction that can take place, as stated in P. N. Rylander, *Hydrogenation Methods* (Best Synthetic Series, published by Academic Press), (1985), page 148.

Patent application EP0409716 discloses the use of Raney nickel associated with a catalyst inhibitor in the presence of iodide. This process presents the drawback in that it uses a catalyst inhibitor. Such an inhibitor should be avoided on an industrial scale.

Patent application WO 02/16322 discloses the use of a metal catalyst (especially palladium) in an alcohol solvent to carry out this reaction. Nevertheless, this process suffers from the disadvantage of dehalogenation reaction due to the high activity of palladium. Furthermore, palladium is a catalyst which is very expensive and which is very sensitive to catalysts poisons, such as the sulfur compounds which are formed during the process leading to the production of 2-cyanopyridines. This hydrogenation process can not be used on an industrial scale.

We have now found a process to prepare 2-aminomethylpyridine derivative which does not possess the above mentioned drawbacks and which is applicable to industrial scale process.

Accordingly, the present invention relates to a process for the preparation of 2-aminomethylpyridine derivative of general formula (I) or a salt thereof:

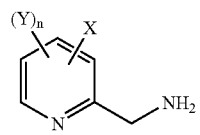
(I)

in which: n represents 0, 1, 2 or 3,

X is halogen atom,

Y may be the same or different and may be a halogen atom, a halogenoalkyl, an alkoxycarbonyl or an alkylsulphonyl;

by hydrogenation of a 2-cyanopyridine derivative of general formula (II) or a salt thereof:

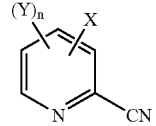
(II)

in which n, X and Y are as defined above, in acetic acid using Raney nickel, at a temperature of from 30° C. to 70° C., under a hydrogen pressure of from 1 to 50 bar.

For the purposes of the present invention:

halogenoalkyl means $C_1$-$C_6$ alkyl moiety substituted by one or more halogen atoms;

alkoxycarbonyl means $C_1$-$C_6$ alkoxycarbonyl. Suitable examples of such a moiety may be methoxycarbonyl, ethoxycarbonyl, n-propoxycarbonyl and i-propoxycarbonyl; alkylsulphonyl means $C_1$-$C_6$ alkysulphonyl;

a halogen atom may be a bromine atom, a chlorine atom, a iodine atom or a fluorine atom.

In the following description Raney nickel will be referred as to Ni—Ra.

The product obtained by the process according to the present invention is the acetate of the compound of general formula (I) which is fully soluble in acetic acid. The catalyst may then be recycled by filtration and the solution of the acetate of the compound of general formula (I) is assayed according to methods well-known by the man ordinary skilled in the art. Yield of acetate of the compound of general formula (I) with respect to 2-cyanopyridine derivative of general formula (II) is usually more than 95%. At 45° C., even with Ni—Ra damp with water, no more than 0.1% yield of dehalogenation product is generally observed in the absence of dehalogenation inhibitors such as KI or KBr usually used with palladium catalysts.

The present invention relates to a process for the preparation of compound of general formula (I). Preferably the different characteristics of compound of formula (I) may be chosen independently from each other as being:

as regards X, X is chlorine;

as regards n, n is 1;

as regards Y, Y is haloalkyl; more preferably, Y is trifluoromethyl.

More preferably, the present invention relates to a process for the preparation of compound of general formula (I) in which:

X is chlorine;

n is 1;

Y is trifluoromethyl.

The process of the present invention is particularly suitable for the preparation of 2-aminomethyl-3-chloro-5-trifluoromethylpyridine.

The process according to the present invention is carried out at a temperature of from 30° C. to 70° C., preferably at a temperature of from 35 to 50° C.

The process according to the present invention is carried out under a pressure of hydrogen of from 1 to 50 bar, preferably under a pressure of from 2 to 30 bar, more preferably under a pressure of from 10 to 20 bar.

The process according to the present invention is carried out in the presence of Ni—Ra. Ni—Ra is preferably introduced in a weight ratio of from 1 to 20% with respect to 2-cyanopyridine derivative of general formula (II).

The process according to the present invention is particularly suitable for the preparation of 2-aminomethyl-3-chloro-5-trifluoromethylpyridine, by hydrogenation of 3-chloro-2-cyano-5-trifluoromethylpyridine in acetic acid using Ni—Ra introduced in a weight ratio of from 1 to 20% with respect to 2-cyanopyridine derivative of general formula (II), at a temperature of from 40 to 50° C., under a hydrogen pressure of from 15 to 20 bar.

The catalyst may be recycled according to methods well known by the man ordinary skilled in the art. Particularly, the catalyst may be easily recycled by filtration.

The process according to the present invention will now be illustrated with reference to the following example.

Example of the Preparation of 2-aminomethyl-3-chloro-5-trifluoromethylpyridine 400 g of acetic acid and 6 g of Ni—Ra (previously washed with water until washings were at a pH of 7) were loaded in a 1 L stainless steel reactor. The reactor was purged with nitrogen and then hydrogen. Heating was applied to the reactor to raise the temperature up to 40° C. and the reactor pressure was raised to 18 bar with hydrogen.

120 g of 3-chloro-2-cyano-5-trifluoromethylpyridine (0.571 mol) were added by pump over 2 hours. The reaction was exothermic and temperature raised to 45° C. Hydrogen consumption was monitored. After 2 hours, no more hydrogen was consumed and the reaction was complete. The mixture was cooled down to 20° C. and then vented off and purged with nitrogen.

The catalyst was filtered. The solution of 2-aminomethyl-3-chloro-5-trifluoromethylpyridine acetic acid salt was assayed by liquid chromatography. 0.558 moles of 2-aminomethyl-3-chloro-5-trifluoromethylpyridine was formed and a 97% yield of 2-aminomethyl-3-chloro-5-trifluoromethylpyridine over 3-chloro-2-cyano-5-trifluoromethylpyridine was obtained. A yield of only 0.05% yield of the dechlorinated analogue was obtained.

The invention claimed is:

1. A process for the preparation of a 2-aminomethylpyridine derivative of general formula (I)

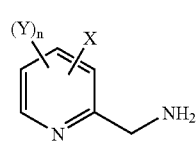

(I)

wherein
n represents 0, 1, 2 or 3,
X is a halogen atom,
each Y, which may be the same or different, is selected from the group consisting of a halogen atom, halogenoalkyl, alkoxycarbonyl, and alkylsulphonyl, or a salt thereof;
comprising hydrogenating a 2-cyanopyridine derivative of general formula (II):

(II)

in which n, X, and Y are as described above,
in acetic acid using Raney nickel, at a temperature of from 30° C. to 70° C., under a hydrogen pressure of from 10 to 20 bar.

2. A process for the preparation of 2-aminomethyl-3-chloro-5-trifluoromethylpyridine comprising hydrogenating 3-chloro-2-cyano-5-trifluoromethylpyridine in acetic acid using Raney nickel introduced in a weight ratio of from 1 to 20% with respect to the 3-chloro-2-cyano-5-trifluoromethylpyridine, at a temperature of from 40 to 50° C., under a hydrogen pressure of from 15 to 20 bar.

3. The process of claim 1 wherein X is chlorine.

4. The process of claim 1 wherein n is 1.

5. The process of claim 1 wherein Y is haloalkyl.

6. The process of claim 5 wherein Y is trifluoromethyl.

7. The process of claim 1 wherein X is chlorine, n is 1 and Y is trifluoromethyl.

8. The process of claim 7 wherein the compound of general formula (I) is 2-aminomethyl-3-chloro-5-trifluoromethylpyridine.

9. The process of claim 1 wherein the temperature is is in the range of from 35 to 50° C.

10. The process of claim 1 wherein the Raney nickel is introduced in a weight ratio of from 1 to 20% with respect to compound of general formula (II).

11. The process of claim 8 wherein the temperature is chosen from 35 to 50° C. and the pressure of hydrogen is chosen from 10 to 20 bar and Raney nickel is introduced in a weight ratio of from 1 to 20% with respect to the compound of general formula (II).

* * * * *